United States Patent
Dybbs (10) Patent No.: US 7,338,508 B2
(45) Date of Patent: *Mar. 4, 2008

(54) OPHTHALMIC SURGICAL SYSTEM AND METHOD

(75) Inventor: Alexander Dybbs, Cleveland, OH (US)

(73) Assignee: AZD Holding, LLC., Beachwood, OH (US)

( * ) Notice: Subject to any disclaimer, the term of this patent is extended or adjusted under 35 U.S.C. 154(b) by 858 days.

This patent is subject to a terminal disclaimer.

(21) Appl. No.: 10/363,340

(22) PCT Filed: Sep. 1, 2001

(86) PCT No.: PCT/US01/27167

§ 371 (c)(1),
(2), (4) Date: Mar. 3, 2003

(87) PCT Pub. No.: WO02/17834

PCT Pub. Date: Mar. 7, 2002

(65) Prior Publication Data

US 2004/0092983 A1    May 13, 2004

Related U.S. Application Data

(60) Provisional application No. 60/229,967, filed on Sep. 1, 2000.

(51) Int. Cl.
*A61F 9/00* (2006.01)
(52) U.S. Cl. .................................. 606/166
(58) Field of Classification Search ............. 606/166, 606/167, 168, 169, 3, 5, 6, 171, 177

See application file for complete search history.

(56) References Cited

U.S. PATENT DOCUMENTS 4,173,980 A    11/1979    Curtin (Continued)

FOREIGN PATENT DOCUMENTS

DE    195 40 439    10/1995

(Continued)

OTHER PUBLICATIONS

Bores, Leo D. M.D., *Refractive Eye Surgery*, Chapter 10 (1993) Published by Blackwell Scientific Publications, Inc.

(Continued)

*Primary Examiner*—Anhtuan T. Nguyen
*Assistant Examiner*—Tuan V. Nguyen
(74) *Attorney, Agent, or Firm*—Renner, Otto, Boisselle & Sklar, LLP (57) ABSTRACT

A system (20) for ophthalmic surgery includes a control assembly (24) placed away from the patient to prevent contamination, and a sterile disposable microkeratome (22) for performing surgery on a patient's eye. The disposable microkeratome is connected to the reusable control assembly by a cable (28). The microkeratome includes a base that sits on the eye, and a carriage that supports and guides a cutting blade as it moves relative to the base. The base includes a main portion that holds the microkeratome on the eye and a handle that extends away from the main portion. The cable is connected to the microkeratome at an end of the handle spaced from the main portion to help maintain the sterility of that portion of the microkeratome.

21 Claims, 9 Drawing Sheets

U.S. PATENT DOCUMENTS

| | | | |
|---|---|---|---|
| 4,570,632 A * | 2/1986 | Woods | 606/166 |
| 4,660,556 A | 4/1987 | Swinger et al. | |
| 4,662,370 A | 5/1987 | Hoffmann et al. | |
| 4,665,914 A | 5/1987 | Tanne | |
| 4,674,503 A | 6/1987 | Peyman et al. | |
| 4,688,570 A | 8/1987 | Kramer et al. | |
| 4,840,175 A | 6/1989 | Peyman | |
| 5,108,412 A | 4/1992 | Krumeich et al. | |
| 5,133,726 A * | 7/1992 | Ruiz et al. | 606/166 |
| 5,215,104 A | 6/1993 | Steinert | |
| 5,342,378 A | 8/1994 | Giraud et al. | |
| 5,496,339 A | 3/1996 | Koepnick | |
| 5,586,980 A | 12/1996 | Kremer et al. | |
| RE35,421 E | 1/1997 | Ruiz et al. | |
| 5,591,174 A | 1/1997 | Clark et al. | |
| 5,595,570 A | 1/1997 | Smith | |
| 5,624,456 A | 4/1997 | Hellenkamp | |
| 5,658,303 A | 8/1997 | Koepnick | |
| 5,690,657 A | 11/1997 | Koepnick | |
| 5,779,723 A * | 7/1998 | Schwind | 606/166 |
| 5,817,115 A | 10/1998 | Nigam | |
| 5,944,731 A * | 8/1999 | Hanna | 606/166 |
| 5,980,543 A | 11/1999 | Carriazo et al. | |
| 5,989,272 A | 11/1999 | Barron et al. | |
| 5,997,559 A | 12/1999 | Ziemer | |
| 6,007,553 A | 12/1999 | Hellenkamp et al. | |
| 6,022,365 A | 2/2000 | Aufaure et al. | |
| 6,042,594 A | 3/2000 | Hellenkamp | |
| 6,126,668 A * | 10/2000 | Bair et al. | 606/166 |
| 6,228,099 B1 * | 5/2001 | Dybbs | 606/166 |
| 6,540,759 B2 * | 4/2003 | Dybbs | 606/166 |

FOREIGN PATENT DOCUMENTS

| | | |
|---|---|---|
| EP | 0873735 | 10/1998 |
| EP | 0895764 | 10/1999 |
| WO | WO 95/20920 | 8/1995 |
| WO | WO 95/28871 | 11/1995 |
| WO | WO 96/21406 | 7/1996 |
| WO | WO 97/20529 | 6/1997 |
| WO | WO 98/27901 | 2/1998 |
| WO | WO 99/26568 | 6/1999 |

OTHER PUBLICATIONS

Kronemyer, Bob, "Advanced microkeratome simplifies ALK", Ocular Surgery News, Dec. 15, 1995.

"LaserSight launches new Ruiz microkeratome", Ocular Surgery News, Nov. 15, 1997.

Black, Harvey, "Newly developed microkeratome may ease LASIK", Ocular Surgery News, Jun. 1, 1996.

Nascimento, Ednei M.D. and Marcos Chaves Barbosa, M.D., "Keratome with clear corneal molder permits good cut for LASIK", Ocular Surgery News, Feb. 1, 1997.

Singer, Henry W., "Superior hinge LASIK with new microkeratome improves safety", Ocular Surgery News, Mar. 15, 1997.

Nordon, Lee T., M.D., "Avoiding LASIK complications takes patience", Ocular Surgery News, International Edition, Mar. 1997.

"Conventional Mechanical Microkeratomes", Ocular Surgery News, Aug. 1, 1998.

Schwind Ophthalmic Technology, flyer for Schwind microkeratome.

* cited by examiner

OPHTHALMIC SURGICAL SYSTEM AND METHOD

RELATED APPLICATIONS

The present application claims priority from U.S. Provisional Application No. 60/229,967, filed Sep. 1, 2000, which is hereby incorporated herein by reference in its entirety.

FIELD OF THE INVENTION

The invention relates to an ophthalmic surgical system and method including a disposable surgical microkeratome and, more particularly, to an automated surgical system and method for using such a device in laser-assisted in situ keratomileusis (LASIK).

BACKGROUND OF THE INVENTION

Ophthalmic surgeons increasingly use new surgical methods and devices for changing the shape of a patient's cornea to correct vision defects, including myopia, hyperopia, and astigmatism. One such device is called a microkeratome which is used, in particular, to cut a corneal flap during performance of LASIK surgery. Unfortunately, there are problems with some of the microkeratomes used in corrective eye surgery.

More particularly, many microkeratomes suffer from one or more disadvantages including, for example, the inability of the microkeratome automatically to cut over a predetermined distance, the microkeratome being made of surgical steel which prevents the surgeon from viewing the cornea as the cutting blade advances, and/or the microkeratome being made of many small metal components which are expensive to produce and assemble. The largest dimension of some microkeratomes is less than about two inches (about five centimeters), meaning that individual components are even smaller. Reassembling such a microkeratome while wearing sterile gloves is particularly difficult. A microkeratome having many small components also is difficult, if not impossible, to clean and sterilize between patients.

Furthermore, some microkeratomes have exposed gears or screw threads which can become contaminated during the surgical operation. The small crevasses in these elements are particularly difficult to maintain in a sterile and smooth working condition. Furthermore, sterility problems have been reported in the field, making complete sterility of the components in the vicinity of the patient more important than ever. Additional problems with some existing microkeratomes are discussed in commonly owned U.S. Pat. No. 6,228,099, the entire disclosure of which is hereby incorporated herein by reference.

One of the better microkeratomes is disclosed in commonly owned International Application No. PCT/US98/24785, published as International Publication No. WO99/26568, which is hereby incorporated herein by reference in its entirety. Although the microkeratome disclosed therein is a significant improvement over microkeratomes at the time, further improvements are desirable.

SUMMARY OF THE INVENTION

The present invention provides a system and method including a microkeratome that is a substantial improvement over existing microkeratomes. According to one aspect of the invention, independent control of the axial movement and transverse movement of a cutting blade in a microkeratome is accomplished through the use of a single control cable that connects the microkeratome to a remotely located control assembly. According to another aspect of the invention, the microkeratome is equipped with a handle that enables connection of the control cable to be effected at a remote location, whereby the microkeratome can be connected to the control cable while maintaining the portion of the microkeratome in the vicinity of the patient's eye in a sterile condition. According to yet another aspect of the invention, the microkeratome includes a base having a main portion for engaging the eye and a hollow handle extending from the main portion, the handle housing a linkage that connects a control shaft to a cutting blade movable relative to the base. According to still another aspect of the invention, the microkeratome includes a biasing device for automatically retracting a carriage from an extended position to a retracted position.

The present invention provides a microkeratome that can be disposable, preassembled and presented in a sterile condition, and a control system that can be reused indefinitely, resulting in greatly reduced cost while providing a superior quality surgical operation.

In particular, the present invention provides a microkeratome for ophthalmic surgery that includes a base, a carriage mounted to the base, and a cutting blade carried in the carriage. The base includes a main portion for mounting on an eye and a handle extending from the main portion to provide for remote connection of a control cable to the microkeratome. The carriage is guided for linear movement in a cutting direction relative to the base and the cutting blade is movable in relative to the carriage. The aforementioned control cable has a control shaft. The control cable is connectable to the base of the microkeratome such that axial movement of the control shaft effects the linear movement of the carriage along the cutting direction, and rotational movement of the shaft effects movement of the cutting blade relative to the carriage.

The present invention also provides a system for ophthalmic surgery that includes a microkeratome and a control assembly for controlling the microkeratome. The control assembly has a drive assembly including the control cable which is connected to the carriage such that axial movement of the control shaft effects movement of the carriage in the cutting direction relative to the base, and rotational movement of the control shaft effects movement of the cutting blade relative to the carriage.

The present invention also provides a method for ophthalmic surgery that includes connecting a control shaft to a microkeratome, axially shifting the control shaft to effect movement of a carriage relative to a base on which it is mounted, and rotating the control shaft to effect movement of a cutting blade relative to the carriage in which it is carried.

Such a method may further include applying the microkeratome to an eye; and independently controlling the movement of the carriage relative to the base and the movement of cutting blade relative to the carriage, disposing of a first microkeratome following a first operation and selecting a second microkeratome for a subsequent operation and/or driving the carriage in a forward direction from a retracted position to an extended position and retracting the carriage from the extended position to the retracted position.

The present invention also provides a system for ophthalmic surgery comprising means for driving a cutting blade for movement, means for supporting the cutting blade relative to an eye, and control means for controlling the means for driving. The control means includes a control cable having a control shaft movable within a sheath, and the means for supporting includes a main portion mountable in the vicinity of an eye and a handle extending from the main portion. The control cable is connectable to the handle, and the control shaft is connectable to the cutting blade such that movement of the control shaft effects movement of the cutting blade.

The present invention further provides a microkeratome for ophthalmic surgery comprising a base, a carriage mounted to the base, and a cutting blade carried in the carriage. The base has a proximal end for engaging an eye and a handle extending away from the proximal end and terminating at a coupling to which at least one control cable having at least one shaft can be connected. The handle houses a linkage extending between the coupling and the carriage for transferring motion from the at least one control shaft to the carriage.

The present invention further provides a microkeratome for ophthalmic surgery wherein the carriage is guided for movement in a cutting direction relative to the base between a retracted position and an extended position and the cutting blade is movable relative to the carriage. The base has associated therewith a biasing member operating to bias the carriage toward the retracted position.

The microkeratome may further have a hollow handle extending away from the main portion, the biasing member being housed within the handle.

The present invention also provides a microkeratome for ophthalmic surgery, wherein the base includes a coupling that includes a first connector for securing the sheath of a control cable and a second connector configured to axially and rotatably interconnect with the end of the control shaft.

The second connector may also be configured to axially and transversely interconnect with the end of the control shaft.

Thus, the present invention provides an improved system, method and microkeratome for ophthalmic surgery. The microkeratome provided by the present invention can be quickly and easily connected to remote drive using a single control cable. The control cable rotates and moves axially within and relative to a sheath without using any gears or other complex components in the microkeratome, thereby minimizing complexity, enhancing the reliability, durability and sterilizable aspects of the microkeratome. This also leads to a microkeratome that is relatively inexpensive to manufacture, allowing the microkeratome to be disposable. In addition, since the drive is located remotely from the microkeratome, it maintains a sterile condition more readily and is reusable.

The foregoing and other features of the invention are hereinafter fully described and particularly pointed out in the claims, the following description and annexed drawings setting forth in detail a certain illustrative embodiment of the invention, this embodiment being indicative, however, of but one of the various ways in which the principles of the invention may be employed.

BRIEF DESCRIPTION OF THE DRAWINGS

FIGS. 4a and 4b are top and cross-sectional side views, respectively, of an alternative to the main portion of the base of FIGS. 3a and 3b, FIG. 4b being a cross-sectional side view as seen along lines 4b-4b of FIG. 4a.

FIGS. 5a and 5c are rear and bottom views, respectively, of a carriage portion of the microkeratome shown in FIG. 2, with FIG. 5b being a cross-sectional view as seen along lines 5b-5b of FIG. 5a.

FIG. 7c is a cross-sectional view of the wedge as seen along lines 7c-7c in FIG. 7a.

DETAILED DESCRIPTION

The present invention provides a system and method of using a disposable microkeratome that facilitates the performance of corrective refractive ophthalmic surgery, particularly keratomileusis, and more particularly laser-assisted in situ keratomileusis (LASIK). Referring now to the drawings in detail, and initially to FIG. 1, the ophthalmic surgical system 20 includes a disposable surgical microkeratome 22 and a remotely located control assembly 24. The control assembly includes a flexible suction line or tube 26 and at least one (preferably only one) control cable 28. The suction tube and the control cable connect the control assembly to the microkeratome for remotely controlling and driving the microkeratome. (As described herein, the term "microkeratome" is used to describe the complete device between the control cable and/or the suction tube and the patient.)

Figure 1:
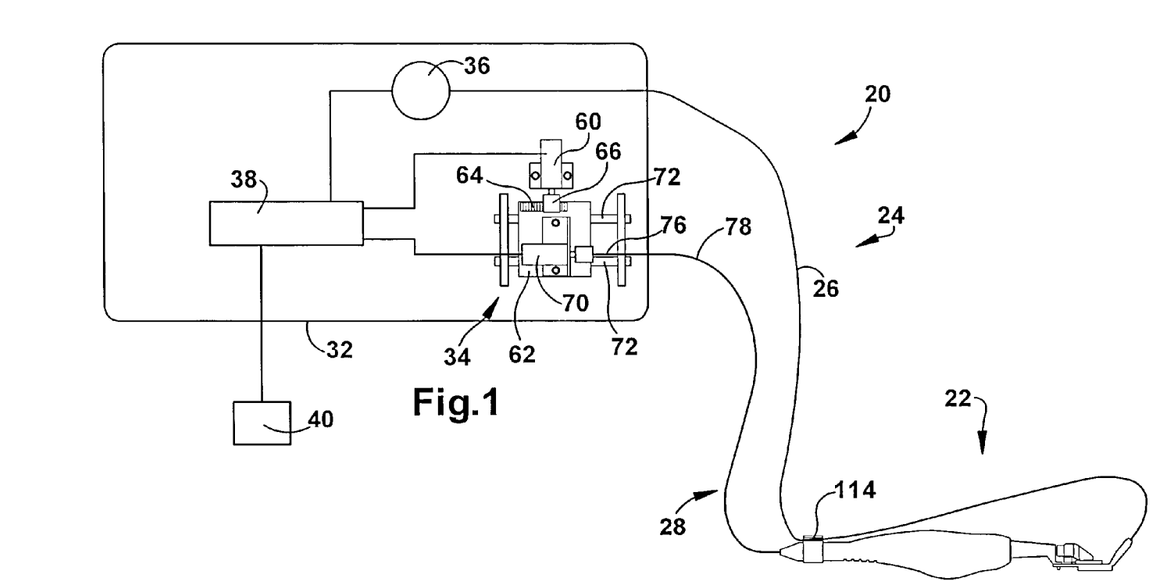
FIG. 1 is a schematic view of the ophthalmic surgical system according to the present invention.

The control assembly 24 is substantially contained within a housing 32 and includes a drive assembly 34, a suction pump 36, and a controller 38. The controller 38 can include an electronic circuit for controlling the operation of the drive assembly and the pump. The control assembly also has one or more input devices 40 connected to the controller, such as a touch screen, an ON/OFF switch, a suction pedal or switch, a two-position drive pedal or switch, and/or a flap length adjustment selector, also referred to as a flap hinge positioning system. The one or more input devices permit the surgeon to control several variables in the operation of the system 20, as further described herein. For more detail concerning the operation of an exemplary control assembly, reference may be had to commonly owned International Application No. PCT/US98/24785, filed Nov. 20, 1998

(published as International Publication No. WO99/26568 on Jun. 3, 1999), which is hereby incorporated herein in its entirety by reference.

The drive assembly 34 is substantially similar to the drive assembly disclosed in the aforementioned International Publication No. WO99/26568, with the exception that the rotary and axial cables in the aforementioned publication have been replaced in the illustrated system with a single control cable that transmits both rotational and axial motion to the microkeratome. The drive assembly 34 includes a linear drive motor 60 connected to slide member 62 by a rack 64 and pinion 66, for example, for moving the slide member through a range of linear motion corresponding to the desired cut length. The slide member is mounted on a pair of parallel rods 72 that act as slide guides for directing or guiding the linear motion of the slide member 62. A rotary drive motor 70 is carried on the slide member for movement therewith. A control cable 28 having a control shaft 76 is connected to the rotary motor 70. Because the rotary drive motor 70 is mounted on the slide member 62, the drive shaft can simultaneously transfer rotational motion (created by the rotary drive motor) and linear axial motion (created by the linear drive motor through the slide member) to the microkeratome.

The control shaft 76 is disposed in a flexible sheath 78 and the shaft and the sheath together form the control cable 28. Consequently, the control cable connects the rotary drive motor 70 and the axial drive motor 60 (through the slide member 62) to the microkeratome 22. The control shaft rotates and/or moves axially within the sheath 70 as the slide member 62 moves through its range of motion.

The control shaft 76 may have a monocoil, double wound or triple wound construction over a central wire or mandrel with the winds pitched in opposite directions to provide torsional rigidity. The triple wound construction provides bi-directional properties as well as flexibility for increased endurance life of the shaft, as compared to a monocoil or double wound construction. The torsional stiffness of the triple wound construction generally is equivalent to or greater than the double wound construction but its flexural stiffness generally is less than about half that of the double wound construction. However, this is desirable because the shaft may rotate in a relatively sharp bend at high speed. The control shaft can be made of stainless steel due to the strength and endurance limit of stainless steel. Furthermore, the exemplary control shaft is coated with a thin wall shrink tubing in order to provide a smooth surface to minimize or eliminate vibration. The inside of the sheath 78 may be coated with a material, such as polytetrafluoroethylene (PTFE), to reduce friction between the sheath and the shaft. Alternatively, the entire sheath may be formed of PTFE. The control shaft is designed to rotate at speeds up to 20,000 revolutions per minute and to provide the necessary torque to drive the microkeratome 22.

Figure 2:
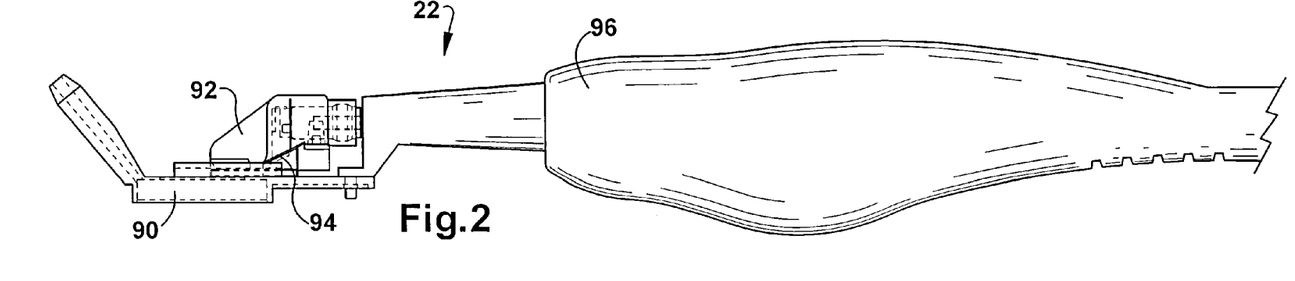
FIG. 2 is a schematic illustration of a microkeratome for use in the system shown in FIG. 1.

An enlarged view of the microkeratome 22 is shown in FIG. 2 and includes a base 90 for mounting the microkeratome on the eye of a patient, a carriage 92 mounted to the base for movement relative to the base, and a cutting blade 94 carried in the carriage. The base includes a main portion and an extension at one end that synergistically provides a handle 96 for holding the microkeratome. The handle holds and guides a control shaft (FIG. 11) that is connected to the carriage for movement therewith. The distal or terminal end of the handle is connectable to the control cable 28 for transferring the motion from the remotely located drive assembly 34 to the cutting blade. The handle includes few, simple components, is disposable as part of the microkeratome, and can be preassembled and connected to the base and the carriage. The handle can be cast or molded as a single piece and may be formed as a unitary part of the base.

Figures 3A, 3B:
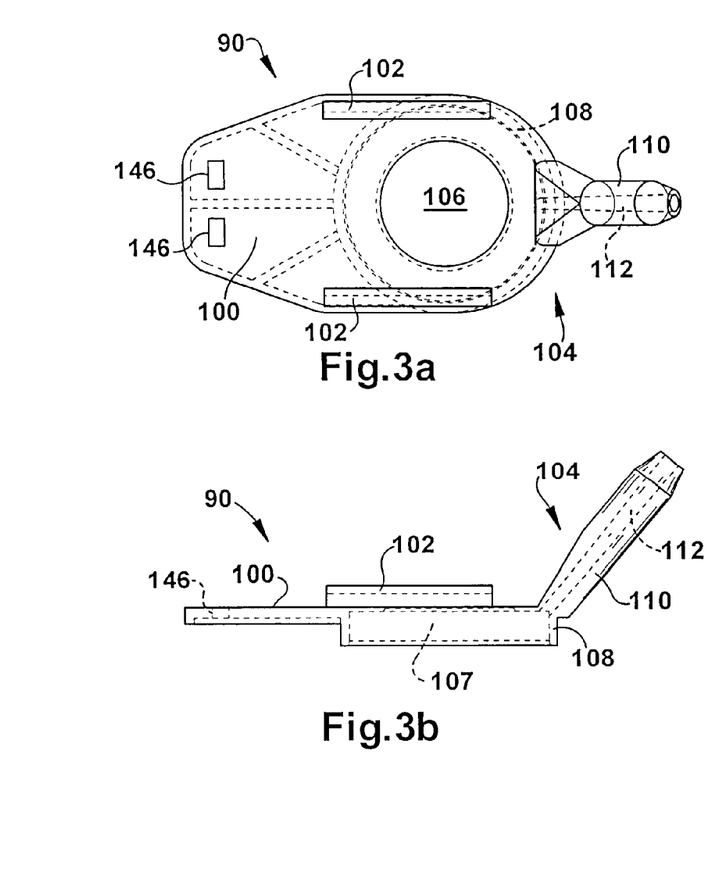
FIGS. 3a and 3b are top and side views, respectively, of a main portion of a base for the microkeratome shown in FIG. 2.

As shown in FIGS. 3a and 3b, the main portion of the base 90 has a substantially flat top surface 100 on which the carriage 92 (FIG. 2) rests. Extending from the top surface, the base includes a pair of spaced apart parallel guides 102. The guides generally have an inverted L-shape and oppose each other to cooperatively form a track or guideway. The guides cooperate with the carriage to restrain and guide the carriage for linear movement along the base in a cutting direction parallel to the length of the guides. The track also functions to hold the carriage to the top surface of the base against any significant separation therefrom, thereby maintaining the carriage in stable sliding engagement with the top surface of the base.

At a front end 104 of the base 90 opposite the handle 96 and between the guides 102, a generally circular opening 106 is provided for receiving a cornea therethrough. The opening communicates through the top surface (and actually top wall) of the base to a substantially cylindrical suction chamber 107 provided at the underside of the base. The chamber is formed in part by a cylindrical suction ring 108 which depends from the top wall of the base and generally is larger than the opening in the base. The suction ring and the opening are adapted for engaging and sealing against the surface of an eye to provide an air tight enclosed space therebetween, or are otherwise configured to form a tight seal with the eye so that a partial vacuum can be drawn to hold the base to the eye. The base 90 also is designed such that when suction is applied to the suction chamber 107, the cornea protrudes through the opening and above the top surface 100 of the base.

As an alternative to the illustrated suction ring, the suction ring may be formed of one or more circumferentially arranged suction devices that hold the microkeratome in a stable relation to the eye.

The base 90 has extending upwardly at the forward end thereof a fixture (or fitting) 110. The illustrated fixture is angled away from the opening 94 to provide an unobstructed view of the cornea. The fixture acts as a suction pipe for attachment of the suction tube 26 (FIG. 1) to the base. The opposite end of the suction tube is connected to the suction pump 36 (FIG. 1). The fitting has a passage 112 extending therethrough to the suction chamber 107. The pump and the tube supply suction to the suction chamber to pump air out of the chamber to create a partial vacuum that retains the base 86 in a stable and fixed position relative to the eye.

The surgeon can use the handle 96 to facilitate positioning the microkeratome on an eye and to hold the microkeratome 22 in place until a partial vacuum is drawn in the suction chamber 107. Consequently, the handle must extend sufficiently for an adult surgeon to place two fingers and a thumb on the handle, and more preferably extends at least about 2 inches (about 5 cm), at least about 3 inches (about 7.6 cm), at least about 4 inches (about 10 cm) or more. Referring briefly to FIG. 1, the suction tube 26 can advantageously be retained adjacent the handle with a clip 114 to help keep the suction tube out of the way during the operation.

Figure 4A:
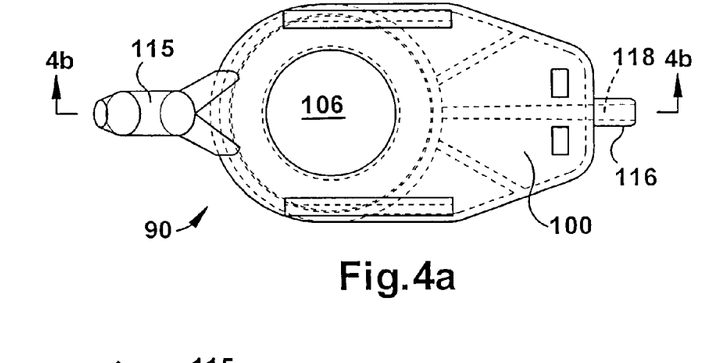
Figure 4B:
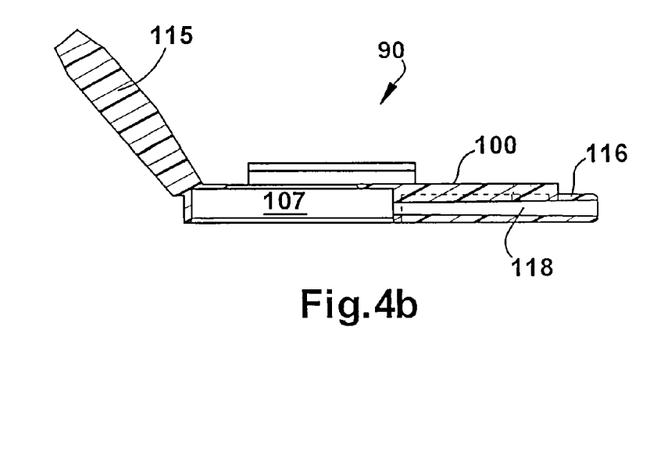

As an alternative to the base 90 shown in FIGS. 3a and 3b, the fixture may be rotated to an alternate position to move the suction tube 26 (FIG. 1) further out of the way, for example as shown in the embodiment illustrated in FIGS. 4a and 4b. In this embodiment, the base 90' is substantially similar to the base 90 shown in FIGS. 3a and 3b, and thus like elements will be identified with like reference numbers.

In this embodiment, the base 90' includes a fixture 115 which is solid, but omitting a passage therethrough to the suction chamber 107. A separate suction pipe 116 is formed in the base with a passage 118 extending from the suction chamber toward a rear end of the base and toward the handle 96 (FIG. 2), away from the fixture. This allows the suction tube to be run underneath the top surface 100 of the base, thereby substantially eliminating any opportunity for the suction tube to obscure the surgeon's view of the operation.

Figure 5A:
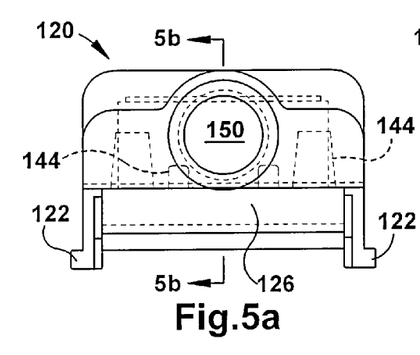
Figure 5B:
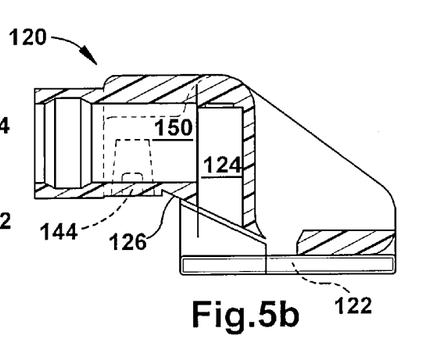
Figure 5C:
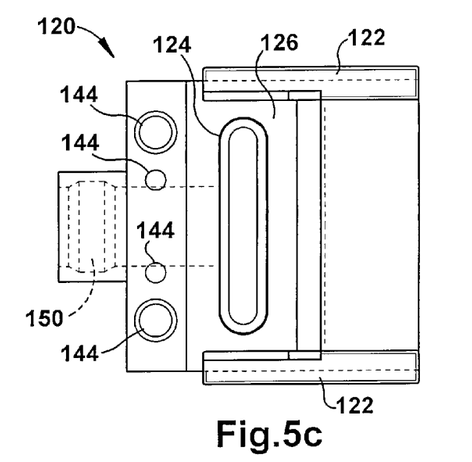

Referring now to FIGS. 5a-5c, the carriage 92 (FIG. 2) includes a cutting head 120 which is substantially similar to the cutting assembly disclosed in the aforementioned international patent publication. A pair of parallel guide rails 122 extend from the sides of the cutting head to cooperatively engage the guides 102 (FIG. 3a) on the base 90 (FIG. 3a).

Figure 6A:
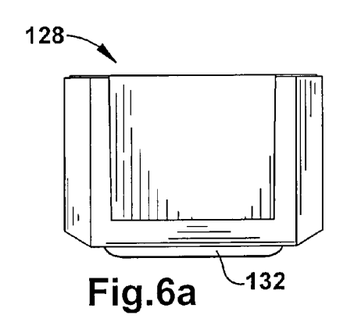
FIGS. 6a-6d are front, top, side, and rear views, respectively, of a blade holder of the microkeratome shown in FIG. 2.
Figure 6B:
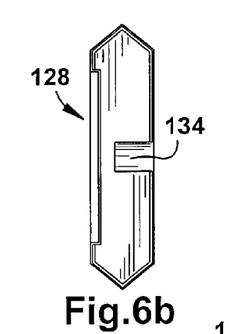
Figures 6C, 6D:
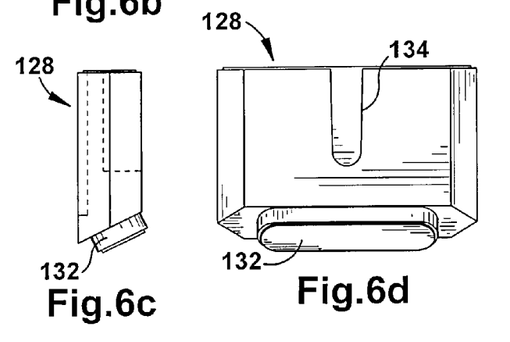

The cutting head 120 has formed therein a substantially vertical slot 124 that opens from an angled blade guide surface 126 underneath the cutting head. The slot sliding receives and guides a blade holder 128 (FIG. 6a) for transverse reciprocating movement therein. The width of the slot is transverse to the direction of the motion of the carriage 92 (FIG. 2) and is wider in the transverse direction than the blade holder to permit the blade holder to oscillate within the slot. The transverse oscillation of the blade holder creates a transverse oscillation of the cutting blade 94 (FIG. 2) which is connected to the blade holder as described below.

The blade holder 128 is illustrated in FIGS. 6a-6d. The blade holder has a protrusion 132 which closely fits through an opening in the cutting blade 94 (FIG. 2). The blade holder also includes a vertical slot 134 which is perpendicular to the width of the blade holder. When the blade holder is assembled in the cutting head 120 (FIG. 3a) the slot 134 is aligned with a substantially horizontal opening or passage 150 (FIGS. 6a-6c) in the cutting head. The passage generally is perpendicular to the slot in the blade holder. Note that the protrusion is angled from the body of the blade holder to extend substantially perpendicularly to the blade guide surface 126 (FIG. 5b) and the cutting blade 94 (FIG. 2) in the illustrated embodiment.

Figure 7A:
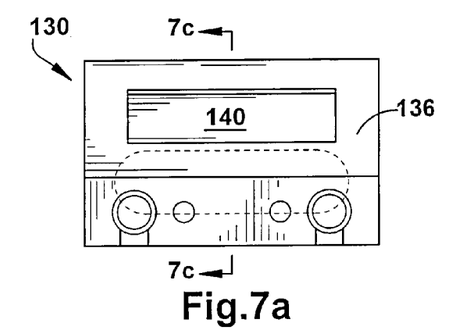
FIGS. 7a and 7b are top and rear views, respectively, of a wedge for use in the microkeratome shown in FIG. 2
Figure 7B:
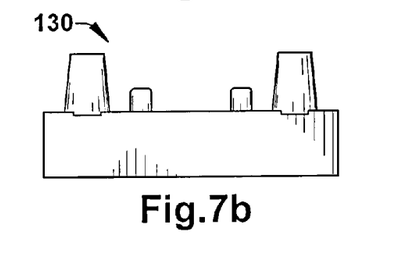
Figure 7C:
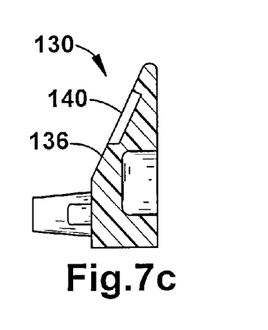
Figure 8:
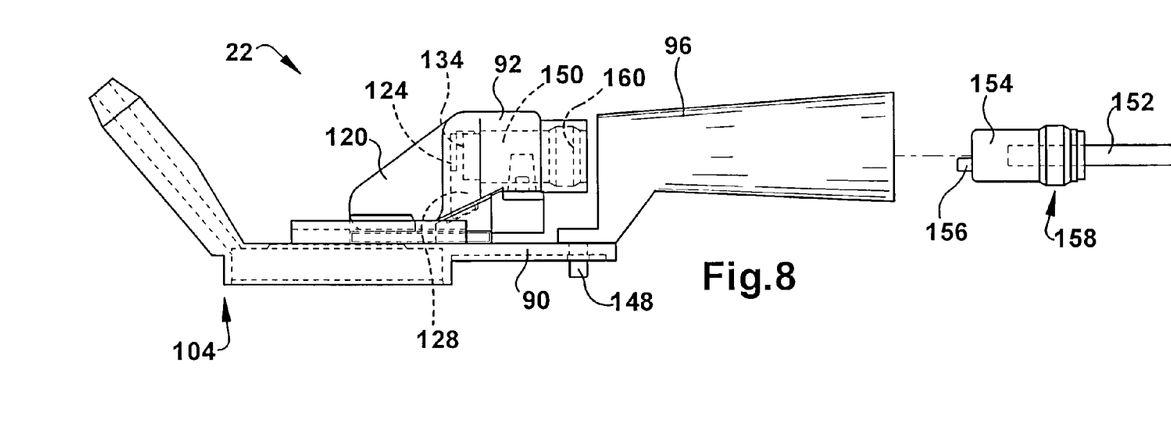
FIG. 8 is a partial enlarged side view of a microkeratome and a forward end of a drive shaft thereof removed therefrom.

The cutting blade 94 (FIG. 2) is held between the angled blade guide surface 126 of the cutting head 120 (FIG. 3a) and a parallel angled top surface of a wedge 130. The wedge is illustrated in FIGS. 7a-7c and supports the cutting blade and the blade holder 128 (FIG. 5a) in the carriage 92 (FIG. 2). The wedge has an approximately triangular cross-section with a thinner portion facing forward. The angled top surface 136 supports the cutting blade as it oscillates with the blade holder. The wedge also includes a transverse recess 140 in the top surface thereof that receives a portion of the protrusion 132 (FIG. 6c) of the blade holder that extends beyond the cutting blade. When the wedge is assembled in the carriage the recess extends substantially coextensively with the vertical slot 124 (FIG. 5b) in the cutting head 120 (FIG. 5b) that receives the blade holder.

The wedge also includes at least one protrusion 142, extending from a top surface. The protrusion is adapted to be press fit or otherwise secured in corresponding recesses 144 (FIG. 5c) in the underside of the cutting head. The recesses cooperate with the protrusions to locate and hold the wedge in place. The wedge locks the cutting blade and the blade holder in the cutting head while allowing the cutting blade and the blade holder to oscillate therebetween. Although the nature of the fit should hold the wedge in place, a surgical adhesive or medical grade epoxy may be used to ensure that the wedge remains in place. Alternative means for positively locating the wedge relative to the carriage and locking it in place may be used as well, or in the alternative.

The carriage (except the cutting blade) and at least the main portion of the base may be composed of transparent materials, such as a transparent molded plastic, to maximize the surgeon's view of the operation.

Referring briefly back to FIGS. 3a and 3b, the base 90 has at a back end thereof one or more openings 146 for fixing the handle 96 thereto by suitable means, such as one or more anchor clips 148 integrally formed in the handle. Any suitable method of attachment may be used, including the illustrated clips which snap into position when pressed into the corresponding openings, as shown more clearly in FIGS. 8-11. As a result, the handle also functions, along with the fixture 110 to retain the carriage 92 (FIG. 2) between the guides 102 and prevent the carriage from disengaging the guides and the base. As noted above, the handle may alternatively be formed as a unitary piece of the base.

As shown in FIG. 2, the handle 96 is connected to both the base 90 and the carriage 92 through a linkage 149. A forward portion of the microkeratome 22 has been enlarged in FIGS. 8-10 to better illustrate the connection between the handle, the base and the carriage, and thus only a portion of the handle is shown.

At a forward end of the handle 96, a drive shaft 152 extends therefrom and is connected to the carriage 92. The drive shaft is removed from the microkeratome 22 in FIG. 8 to more clearly illustrate its shape. The drive shaft has a fitting 154 on a proximal end thereof, from which an eccentric 156 extends. The fitting passes through the horizontal passage 150 in the carriage to extend the eccentric into the slot 124 in the cutting head 120 to engage the vertical slot 134 in the blade holder 128. The fitting also has a distended portion 158 which has a greater thickness than the rest of the fitting and the drive shaft. The cutting head has a corresponding annular recess 160 in the passage 150. The fitting can be press fit into the passage until the distended portion of the fitting snaps or locks the fitting into the annular recess, thereby securing the fitting in the carriage such that it can freely rotate while providing a positive connection between the drive shaft and the carriage for advancing and retracting the carriage along the base 90. Alternative means for connecting the drive shaft to the carriage may be used, including a bayonet coupling, for example. However, the illustrated method requires fewer parts and is faster and less expensive to assemble.

Figure 9:
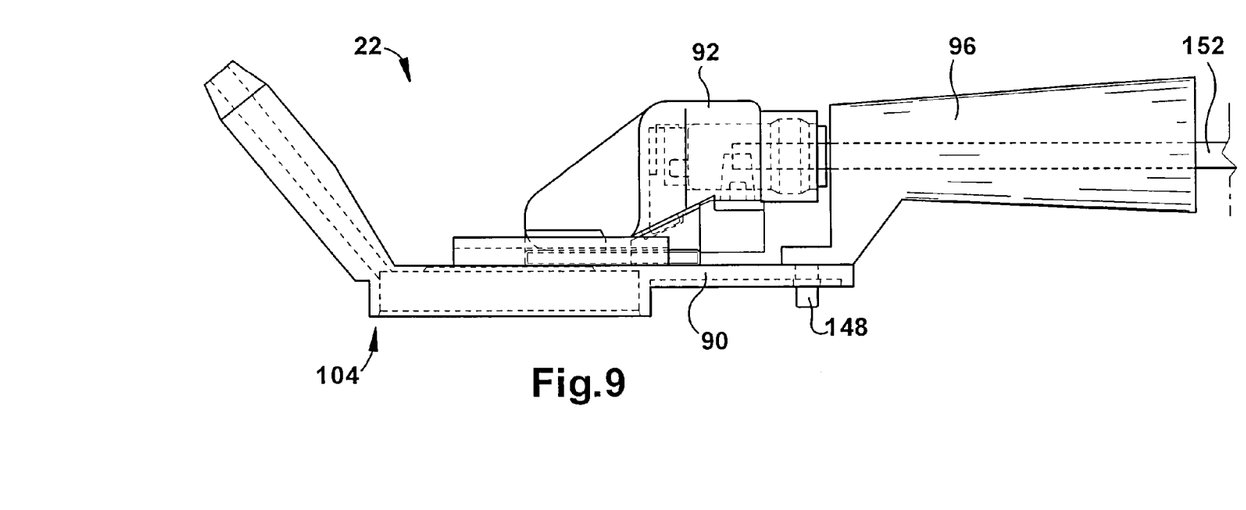
FIG. 9 is a partial enlarged side view of the microkeratome shown in FIG. 2 in a retracted position.
Figure 10:
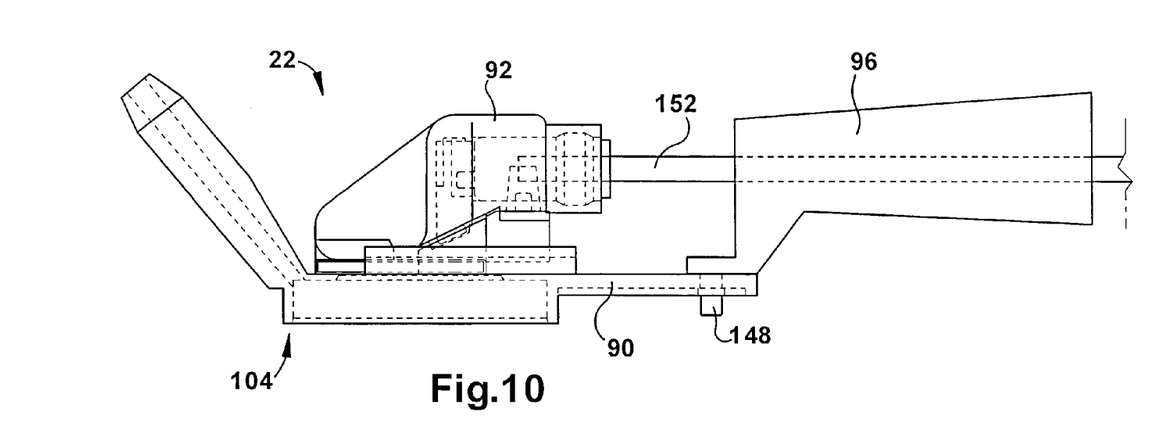
FIG. 10 is a partial enlarged side view of the microkeratome shown in FIG. 2 in an advanced position.

In connecting the handle 96 to the base 90 and the carriage 92, the carriage generally is advanced toward the forward end 104 of the base toward its distal portion, and the drive shaft 152 is extended from the forward or proximal end of the handle to snap the fitting 154 thereon into the passage 150 in the carriage. The anchor clips 148 on the handle are then snapped into the openings 146 (FIG. 3a) in the base, as shown in FIG. 10. The drive shaft can then be retracted to move the carriage toward its proximal position at the rear of the base, as shown in FIG. 9. The assembly of the microkeratome 22 is thus complete.

Figure 11:
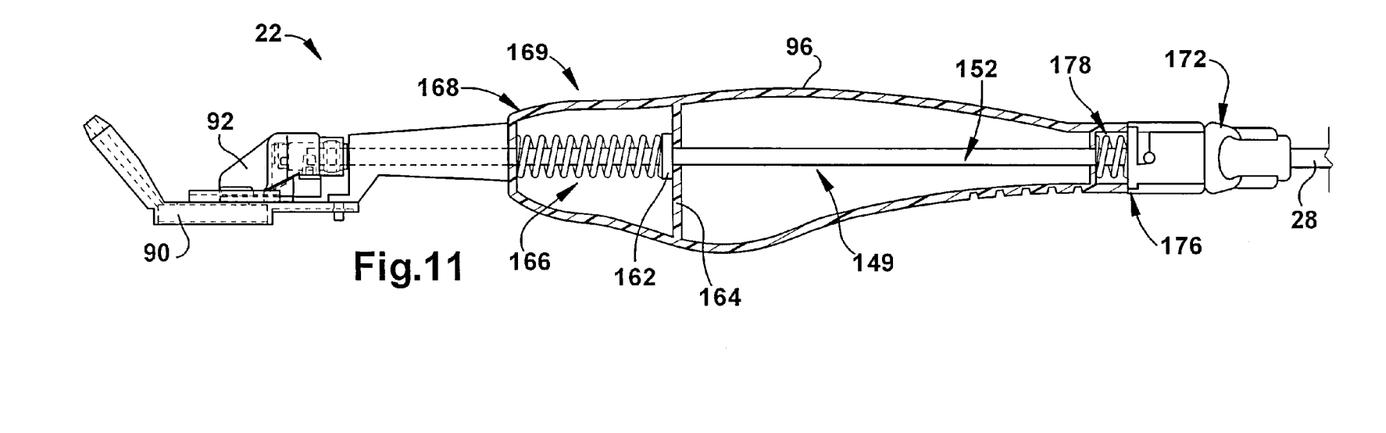
FIG. 11 is a partial cut away side view of an extended portion of a base of the microkeratome of FIG. 2.

An assembled microkeratome 22 is shown in FIG. 11. As can be seen, the drive shaft 152 generally is enclosed within the hollow handle 96, which can be formed economically of a molded plastic material. The drive shaft can be a flexible shaft, similar to the control shaft 76 (FIG. 1) of the control cable 28, or it can be formed of a solid rod or bar, such as a metal rod. The fitting 154 (FIG. 8) at the forward end of the drive shaft can be formed of a metal or other material which can be economically formed into the desired shape to perform the intended function of positively engaging the carriage 92 and transmitting rotational motion as well as forward and reverse motion to the carriage.

As shown in FIG. 11, the drive shaft 152 may include an annular flange 162 at an intermediate point along the length of the shaft. The flange is shown resting against a forward side of a retaining wall (or retaining members) 164 extending into the interior of the handle 96. From the annular flange, the drive shaft extends through a compression spring 166, such as a nylon spring, and a forward wall 168 in the handle. The flange, the forward and retaining walls, and the spring cooperate to form an automatic return device 169 or biasing element. The spring acts on the flange to resist forward movement of the drive shaft and biases the flange toward the retaining wall when insufficient force is applied to the drive shaft to overcome the spring force. As a result, the microkeratome 22 having such a handle automatically retracts the drive shaft and the carriage from its extended position to its retracted position under the influence of the spring at the end of the cutting operation when the forward power is reduced. Automatic retraction is particularly advantageous when there is a loss of power to the system.

Figure 12:
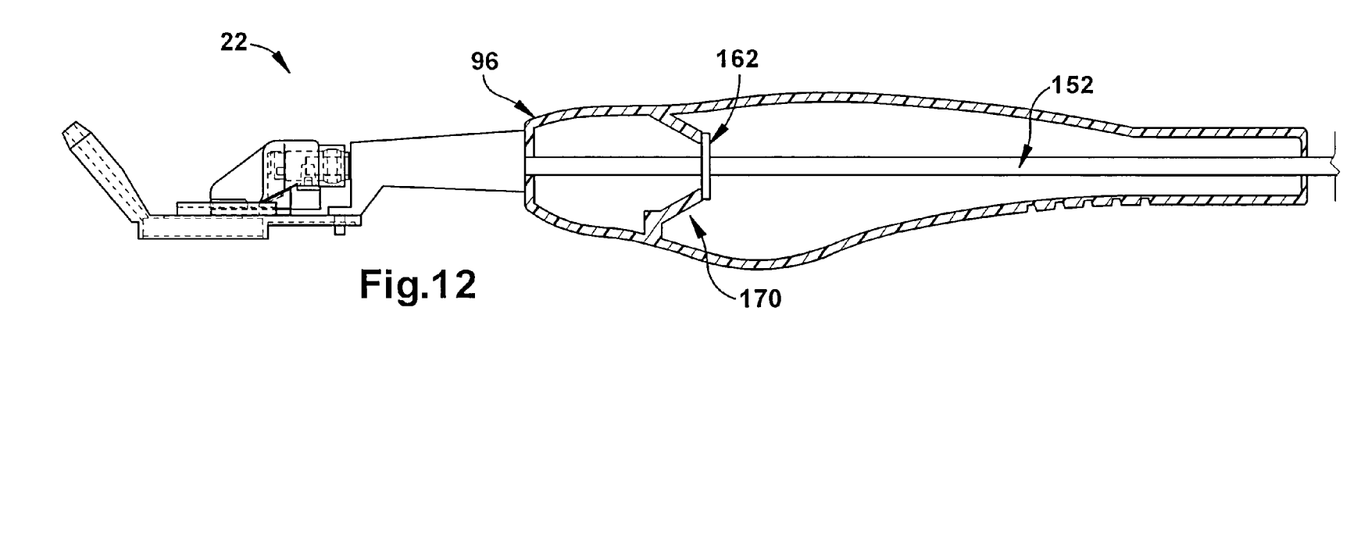
FIG. 12 is a partial cut away side view of an alternative embodiment of the base.

An alternative embodiment of an automatic return device is illustrated in FIG. 12, where angled wall portions 170 extend into the interior of the handle 96. The wall portions function as spring-like members which simultaneously resist the passage of the annular flange 162 on the drive shaft 152 toward the forward end of the handle and automatically retract the drive shaft and the carriage 92 in the event of a loss of power. Consequently, in this embodiment the wall portions 170 combine the functions of the compression spring 166 and the retaining wall 164 in the embodiment shown in FIG. 11 In either embodiment, the drive shaft 152 transmits the rotational and axial motion of the control shaft 76 from the control cable 28 to the carriage 92. The control cable is connected to the rear of the handle 96. Any means for connecting the control cable to the drive shaft is acceptable, as long as it provides a positive connection for the transmission of rotational motion and both forward and reverse axial motion.

One type of connection is shown in the embodiments illustrated in FIGS. 11, and 13a-14b, for example. The sheath 78 of the control cable 28 is held in a fitting 172 on the end thereof and through which the control shaft 76 passes. The end of the fitting abuts the rear end of the handle 96 and is attached thereto by a bayonet coupling 176, for example, held in place by another spring 178. The control shaft passes through the fitting and the spring into the handle where it abuts and engages the rear end of the drive shaft 152. The positive contact between the control shaft and the drive shaft permits the drive shaft to transmit forward axial motion of the control shaft to the carriage, with the automatic return device 169 biasing the drive shaft toward the control shaft to provide reverse axial motion of the drive shaft and retraction of the carriage 92.

Figure 13A:
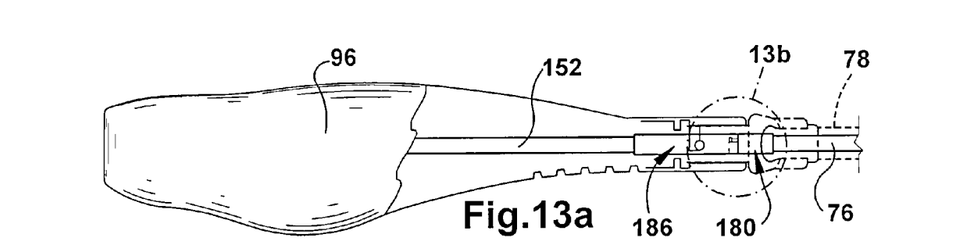
FIGS. 13 and 13a are partial views of a handle portion of the base and a connector for connecting the base to the control cable.
Figure 13B:
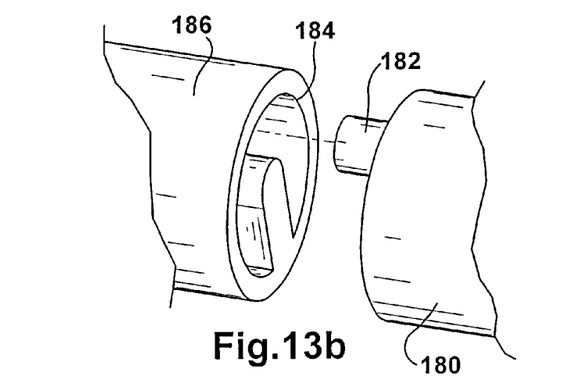
Figure 14A:
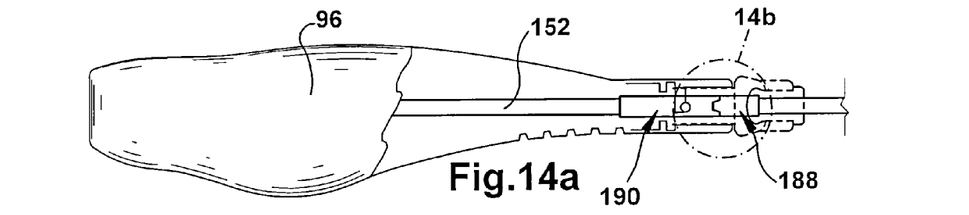
FIGS. 14a and 14b illustrate an alternative connection between the base and the control cable.
Figure 14B:
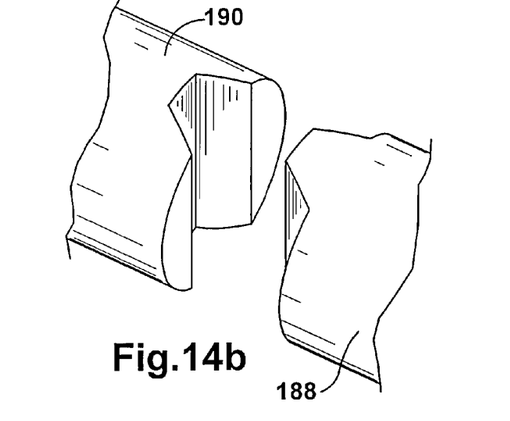

In FIGS. 13a and 13b, one configuration is shown for transferring rotational motion from the control shaft 76 to the drive shaft 152. In this embodiment, the control shaft has a fitting or key 180 on an end thereof with an eccentric 182 which mates with a semi-circular slot 184 in a corresponding fitting 186 on the rear end of the drive shaft. The slot 184 can be larger than the eccentric 182 to facilitate locating the eccentric therein. Since the control shaft generally only rotates in one direction, a loose fit can be utilized between the eccentric and the slot. Another embodiment is illustrated in FIGS. 14a and 14b, wherein the fitting 188 on the control shaft and the fitting 190 on the drive shaft have male/female faces which mate together to provide a positive interlock for transferring rotational motion. However, both of these embodiments require the use of an automatic return device, such as those described above with respect to FIGS. 11 and 12.

An alternative means for connecting the control cable 28 to the microkeratome 22 (FIG. 11) is illustrated in FIGS. 15a-15d. This type of connection does not require internal components in the handle 96 other than the drive shaft 152, and does not require the drive shaft to have an intermediate flange, thereby reducing manufacturing costs, while at the same time improving the reliability of the system and providing positive control over the return motion of the carriage 92 (FIG. 11). In this embodiment fittings 192, 194 on the drive shaft and the control shaft, respectively, partially axially and transversely overlap and interlock to advantageously provide positive transfer of rotational motion as well as both forward and reverse axial motion.

Figure 15A:
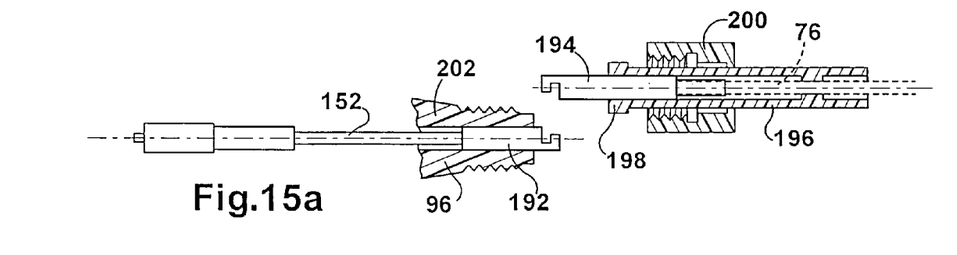
FIGS. 15a-15d show sequential steps in connecting yet another connection between the base and the control cable.
Figure 15B:
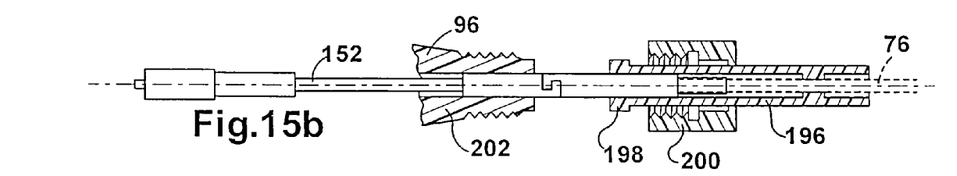

In this embodiment the sheath 78 of the control cable 28 is swaged into a cylindrical fitting 196 through which the control shaft 76 extends. The distal end of the fitting has an annular flange 198 which retains a threaded nut 200 which fits over the fitting and the sheath. The nut is retracted, as shown in FIGS. 15a and 15b, for the connection of the control shaft fitting 194 to the drive shaft fitting 192. The fitting on the drive shaft protrudes from the handle 96 and has a shape which partially overlaps and mates with the fitting on the control shaft. The control shaft can be extended to push the drive shaft into the handle and to draw the sheath fitting 196 toward the handle.

Figure 15C:
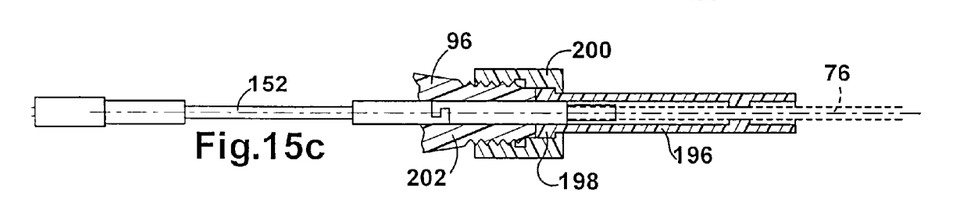
Figure 15D:
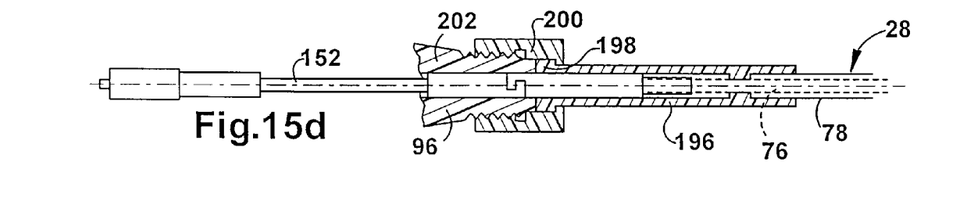

A portion 202 of the rear end of the handle 96 also is threaded, or includes a threaded part mounted thereto, which mates with the threaded nut 200 on the control cable. Once the control shaft 76 and the drive shaft 152 are connected, the control shaft is advanced to move the sheath fitting 196 and the nut into engagement with the rear end of the handle, and the threaded parts are screwed together, as shown in FIG. 15c, to secure the sheath to the handle and to lock the shafts together. The control shaft can then be retracted to positively retract the drive shaft along with it, as shown in FIG. 15d.

Referring now to FIGS. 9 and 10 as well, in order to remotely drive the carriage 92 relative to the base 90 (FIG. 1), the control cable 28 (FIG. 1) relies on relative movement between the control shaft 76 and the sheath 78, with no resulting change in the displacement of the end of the sheath from the base of the microkeratome 22 as the control shaft moves axially within the sheath. In this embodiment, the sheath is held in the fitting, which is positively secured to the rear end of the handle, which in turn is connected to the base. As a result, forward and reverse axial motions of the control shaft moving through the sheath results in forward and reverse motion of the drive shaft and the carriage without the necessity for any gears or rotational motion on the part of the control shaft to effect movement of the carriage 92 relative to the base 90 (FIG. 1).

In addition, the rotational motion of the control shaft 76 is transmitted to the carriage 92 (FIG. 11) by the drive shaft 152 where the cutting head 120 (FIG. 5b), the blade holder 128 (FIG. 6c), and the wedge 130 (FIG. 7a) cooperate to transform the rotational motion into an oscillating motion for driving the cutting blade 94 (FIG. 2) in an oscillating side-to-side motion.

The surgeon or other member of the surgical staff will select the optimum microkeratome from a plurality of microkeratomes, with different microkeratomes providing different size openings in the base and/or providing for different depths of cut. The different microkeratomes are useful for accomodating different size eyes and different depths of cut relative to the different size eyes. The microkeratome comes preassembled and requires no assembly in the operating room. Someone from the surgical staff removes the packaging and connects the microkeratome to the control assembly. The assembler generally double-gloves to maintain sterility, removing one set of gloves after touching reusable components of the control assembly. A new, and sterile, suction tube is connected to the fixture and the suction pump, and the control cable is connected to the handle of the microkeratome. The microkeratome can be handed to the surgeon and the surgeon can position the microkeratome on the eye by holding the handle without contacting any other component of the system. Operation of the microkeratome is substantially automatic and proceeds in substantially the same manner as the operation of the microkeratome described in the aforementioned Published Application No. WO 99/26568. The surgeon can control the microkeratome with foot pedals, without touching the control assembly with his hands, further maintaining sterility. Once the operation is complete, the microkeratome can be disconnected from the control assembly and discarded. A new microkeratome is selected for a subsequent operation.

The control assembly includes components that are expensive to produce and are intended to be reused for surgery on many patients, whereas the microkeratome includes relatively inexpensive components and is intended to be used for a single eye of a single patient and then discarded. Because the control assembly is removed from the patient and thus away from the surgical area, contamination of the control assembly by the patient and vice versa, is minimized or prevented.

Although the present invention has been described with reference to an embodiment that uses a single cable, the invention also includes a microkeratome having a handle for connecting more than one cable. For example, the invention includes a microkeratome connectable to a first cable used to control movement of the blade relative to the carriage and a second cable used to control movement of the carriage relative to the base.

An exemplary microkeratome is formed primarily of a few molded plastic parts that are easy to manufacture and assemble such that the microkeratome is inexpensive to produce. Consequently the microkeratome may be considered disposable, thereby obviating problems of cleaning and sterilizing the microkeratome between patients. The microkeratome is provided completely assembled, sterilized, and ready for use. Since only the microkeratome comes into contact with the patient, the microkeratome does not require extensive assembly by the surgical staff immediately prior to surgery, and the microkeratome is only used once, the surgical area is more easily and more effectively maintained in a clean and sterile condition. Maintaining such a high degree of confidence in the sterility of a microkeratome has been a problem that is problem for which the present invention provides an improved solution.

In summary, since the axial and rotary motors are independently controllable, the system can independently control the oscillation and speed of advance of the cutting blade. The system of the present invention also advantageously uses a single control cable to drive the microkeratome. In addition, the microkeratome includes a handle that facilitates a quick connection between the carriage and the control cable at a location remote from the main portion of the base, and thus the patient's eye. The present invention also provides a microkeratome having means for automatically retracting the cutting blade, a particular advantage in the event of a sudden loss of power. The present invention clearly provides significant improvements over the prior art.

Although the invention has been shown and described with respect to certain illustrated embodiments, equivalent alterations and modifications will occur to others skilled in the art upon reading and understanding the specification and the annexed drawings. In particular regard to the various functions performed by the above described integers (components, assemblies, devices, compositions, etc.), the terms (including a reference to a "means") used to describe such integers are intended to correspond, unless otherwise indicated, to any integer which performs the specified function (i.e., that is functionally equivalent), even though not structurally equivalent to the disclosed structure which performs the function in the herein illustrated embodiments of the invention. In addition, while a particular feature of the invention may have been described above with respect to only one of several illustrated embodiments, such a feature may be combined with one or more other features of the other embodiment, as maybe desired and advantageous for any given or particular application.

What is claimed is:

1. A microkeratome for ophthalmic surgery comprising a base, a carriage mounted to the base, and a cutting blade carried in the carriage, the carriage being guided for movement in a cutting direction relative to the base and the cutting blade being movable relative to the carriage in a direction transverse the cutting direction, and the base being configured for connection to a control cable having a sheath and a control shaft movable within the sheath such that rotational movement of the control shaft about its longitudinal axis effects the movement of the cutting blade relative to the carriage and linear movement of the control shaft along its longitudinal axis effects movement of the carriage relative to the base in the cutting direction, wherein the base includes a suction ring for coupling to an eye and a handle extending from the suction ring, and the handle includes a coupling and a linkage extending between the coupling and the carriage for transferring motion from the control shaft of the cable to the carriage and the cutting blade.

2. The microkeratome of claim 1, wherein the handle has a length sufficient to enable grasping by the thumb and at least two fingers of an adult human hand.

3. The microkeratome of claim 2, wherein the handle has a remote end spaced from the suction ring by at least about 2 inches (about 5 cm).

4. The microkeratome of claim 1, wherein the handle extends in a direction substantially perpendicular to the center axis of the suction ring.

5. The microkeratome of claim 1, wherein the base has an opening extending from a top surface of the base to the suction ring on a bottom side of the base, the suction ring being adapted to be seated on an eye such that at least a portion of a cornea of the eye passes through the opening and protrudes above the top surface of the base.

6. The microkeratome of claim 5, wherein the base includes a fixture having a passage extending therethrough and connected to the suction ring and the fixture is connectable to a vacuum source.

7. The microkeratome of claim 5, wherein the suction ring includes a continuous circumferential wall extending generally parallel to a center axis of the suction ring.

8. The microkeratome of claim 1, wherein the base includes at least one guide which retains the carriage adjacent the base and which guides the movement of the carriage in the cutting direction.

9. The microkeratome of claim 1, wherein the base has associated therewith a biasing member operating to bias the carriage toward the retracted position.

10. A system for ophthalmic surgery comprising a microkeratome as set forth in claim 1, and a control assembly for controlling the microkeratome, the control assembly having a drive assembly including a control cable having a control shaft which is connected to the carriage via the linkage such that the linear movement of the control shaft effects the movement of the carriage in the cutting direction relative to the base and the rotational movement of the control shaft effects the movement of the cutting blade relative to the carriage.

11. The system of claim 10, wherein the control cable includes a sheath in which the control shaft moves, the sheath being connected to the base such that the linear movement of the control shaft relative to the sheath imparts linear movement to the carriage.

12. The system of claim 10, wherein the control assembly includes a suction device for supplying suction pressure to the microkeratome, the suction device being connected to the microkeratome for generating at least a partial vacuum in a suction portion of the base for holding the base to an eye.

13. The system of claim 10, further comprising a plurality of microkeratomes which provide for respective different depths of cut, the microkeratome connected to the control assembly being selected from the plurality of microkeratomes.

14. The system of claim 10, wherein the base has an opening extending from a top surface of the base to the suction ring on a bottom side of the base, the suction ring being adapted to be seated on an eye such that at least a portion of a cornea of the eye passes through the opening and protrudes above the top surface of the base.

15. The system of claim 14, further comprising a plurality of microkeratomes which provide for different sizes of openings, the microkeratome connected to the control assembly being selected from the plurality of microkeratomes.

16. The system of claim 10, wherein the microkeratome is disposable and the control assembly is reusable.

17. The system of claim 10, wherein the drive assembly further includes a slide member movable through a range of linear motion by a linear motor; and a rotary motor mounted on the slide member for movement therewith;

wherein the rotary motor is connected to the microkeratome through the shaft.

18. A microkeratome for ophthalmic surgery comprising a base, a carriage mounted to the base, and a cutting blade carried in the carriage, the carriage being guided for movement in a cutting direction relative to the base and the cutting blade being movable relative to the carriage in a direction transverse the cutting direction, the base having a proximal end for engaging an eye and a handle extending away from the proximal end, the handle having a coupling to which at least one control cable can be connected, the at least one control cable including a sheath and a shaft movable within the sheath and the handle housing a linkage extending between the coupling and the carriage for transferring rotational motion of the control shaft about a longitudinal axis to effect movement of the cutting blade relative to the carriage and for transferring linear movement of the control shaft along the longitudinal axis to effect movement of the carriage relative to the base.

19. A microkeratome as set forth in claim 9, wherein the biasing member is housed within the handle.

20. The microkeratome of claim 18, wherein the coupling includes a first connector for securing the sheath to the base and a second connector configured to interconnect the end of the shaft to the linkage to transfer rotational movement of the shaft about a longitudinal axis to the carriage to effect movement of the cutting blade relative to the carriage and to transfer linear movement of the shaft along the longitudinal axis to the carriage to effect movement of the carriage relative to the base.

21. A microkeratome as set forth in claim 20, wherein the second connector is configured to axially and transversely interconnect with the end of the shaft.

* * * * *